United States Patent
Crowe et al.

(10) Patent No.: US 7,192,553 B2
(45) Date of Patent: Mar. 20, 2007

(54) IN SITU STERILIZATION AND DECONTAMINATION SYSTEM USING A NON-THERMAL PLASMA DISCHARGE

(75) Inventors: Richard Crowe, Hazlet, NJ (US); George Korfiatis, Basking Ridge, NJ (US); Sergei Babko-Malyi, West Windsor, NJ (US)

(73) Assignees: Plasmasol Corporation, Hoboken, NJ (US); Stevens Institute of Technology, Hoboken, NJ (US)

( * ) Notice: Subject to any disclaimer, the term of this patent is extended or adjusted under 35 U.S.C. 154(b) by 686 days.

(21) Appl. No.: 10/287,771

(22) Filed: Nov. 4, 2002

(65) Prior Publication Data

US 2003/0132100 A1 Jul. 17, 2003

Related U.S. Application Data

(63) Continuation-in-part of application No. 09/738,923, filed on Dec. 15, 2000, now Pat. No. 6,818,193.

(60) Provisional application No. 60/369,654, filed on Apr. 2, 2002, provisional application No. 60/336,868, filed on Nov. 2, 2001, provisional application No. 60/336,866, filed on Nov. 2, 2001, provisional application No. 60/171,324, filed on Dec. 21, 1999, provisional application No. 60/171,198, filed on Dec. 15, 1999.

(51) Int. Cl.
*A61L 2/00* (2006.01)

(52) U.S. Cl. .......................... 422/23; 422/22; 422/28; 422/29

(58) Field of Classification Search .................. 422/22, 422/23, 28, 29
See application file for complete search history.

(56) References Cited

U.S. PATENT DOCUMENTS 3,594,065 A 7/1971 Marks (Continued)

FOREIGN PATENT DOCUMENTS

EP 1 084 713 A1 3/2001

(Continued)

OTHER PUBLICATIONS

Vidmar, R. J., "On the Use of Atmospheric Pressure Plasma as Electromagnetic Reflectors and Absorbers", *IEEE Transactions on Plasma Science*, vol. 18 No. 4, Aug. 1990.

(Continued)

*Primary Examiner*—Krisanne Jastrzab
(74) *Attorney, Agent, or Firm*—Darby & Darby (57) ABSTRACT

A sterilization and decontamination system in which a non-thermal plasma discharge device is disposed upstream of a suspension media (e.g., a filter, electrostatic precipitator, carbon bed). The plasma discharge device generates a plasma that is emitted through apertures (e.g., capillaries or slits) in the primary dielectric. Plasma generated active sterilizing species when exposed to contaminants or undesirable particulate matter is able to deactivate or reduce such matter in contaminated fluid stream and/or on objects. Thus, the undesirable contaminants in the fluid to be treated are first reduced during their exposure to the plasma generated active sterilizing species in the plasma region of the discharge device. Furthermore, the plasma generated active sterilizing species are carried downstream to suspension media and upon contact therewith deactivate the contaminants collected on the suspension media itself. Advantageously, the suspension media may be cleansed in situ. To increase the sterilization efficiency an additive, free or carrier gas (e.g., alcohol, water, dry air) may be injected into the apertures defined in the primary dielectric. These additives increase the concentration of plasma generated active sterilizing agents while reducing the byproduct of generated undesirable ozone pollutants. Downstream of the filter the fluid stream may be further treated by being exposed to a catalyst media or additional suspension media to further reduce the amount of undesirable particulate matter.

22 Claims, 6 Drawing Sheets

U.S. PATENT DOCUMENTS

| | | | |
|---|---|---|---|
| 3,948,601 A | 4/1976 | Fraser et al. | |
| 4,147,522 A | 4/1979 | Gonas et al. | |
| 4,265,747 A * | 5/1981 | Copa et al. | 210/758 |
| 4,357,151 A | 11/1982 | Helfritch et al. | |
| 4,643,876 A | 2/1987 | Jacobs et al. | |
| 4,698,551 A | 10/1987 | Hoag | 313/619 |
| 4,756,882 A | 7/1988 | Jacobs et al. | |
| 4,780,277 A * | 10/1988 | Tanaka et al. | 422/4 |
| 4,818,488 A | 4/1989 | Jacob | |
| 4,885,074 A | 12/1989 | Susko et al. | 204/298 |
| 4,898,715 A | 2/1990 | Jacob | |
| 4,931,261 A | 6/1990 | Jacob | |
| 5,033,355 A | 7/1991 | Goldstein et al. | 89/8 |
| 5,062,708 A | 11/1991 | Liang et al. | 356/316 |
| 5,084,239 A | 1/1992 | Moulton et al. | |
| 5,115,166 A | 5/1992 | Campbell et al. | |
| 5,178,829 A | 1/1993 | Moulton et al. | |
| 5,184,046 A | 2/1993 | Campbell | |
| 5,186,893 A | 2/1993 | Moulton et al. | |
| 5,200,146 A * | 4/1993 | Goodman | 422/23 |
| 5,262,125 A | 11/1993 | Goodman | |
| 5,288,460 A | 2/1994 | Caputo et al. | |
| 5,325,020 A | 6/1994 | Campbell et al. | |
| 5,376,332 A | 12/1994 | Martens et al. | |
| 5,387,842 A | 2/1995 | Roth et al. | |
| 5,408,160 A | 4/1995 | Fox | |
| 5,413,758 A | 5/1995 | Caputo et al. | |
| 5,413,759 A | 5/1995 | Campbell et al. | |
| 5,413,760 A | 5/1995 | Campbell et al. | |
| 5,414,324 A | 5/1995 | Roth et al. | |
| 5,451,368 A | 9/1995 | Jacob | |
| 5,458,856 A * | 10/1995 | Marie et al. | 422/186 |
| 5,472,664 A | 12/1995 | Campbell et al. | |
| 5,476,501 A | 12/1995 | Stewart et al. | 607/127 |
| 5,482,684 A | 1/1996 | Martens et al. | |
| 5,498,526 A | 3/1996 | Caputo et al. | |
| 5,549,735 A | 8/1996 | Coppom | |
| 5,593,476 A | 1/1997 | Coppom | |
| 5,593,550 A | 1/1997 | Stewart et al. | 204/164 |
| 5,593,649 A | 1/1997 | Fisher et al. | |
| 5,594,446 A | 1/1997 | Vidmar et al. | 342/1 |
| 5,603,895 A | 2/1997 | Martens et al. | |
| 5,620,656 A | 4/1997 | Wensky et al. | |
| 5,637,198 A | 6/1997 | Breault | |
| 5,645,796 A | 7/1997 | Caputo et al. | |
| 5,650,693 A | 7/1997 | Campbell et al. | |
| 5,667,753 A | 9/1997 | Jacobs et al. | |
| 5,669,583 A | 9/1997 | Roth | |
| 5,686,789 A | 11/1997 | Schoenbach et al. | |
| 5,695,619 A | 12/1997 | Williamson et al. | |
| 5,733,360 A | 3/1998 | Feldman et al. | |
| 5,752,878 A * | 5/1998 | Balkany | 454/236 |
| 5,753,196 A | 5/1998 | Martens et al. | |
| 5,872,426 A | 2/1999 | Kunhardt et al. | 313/582 |
| 5,876,663 A | 3/1999 | Laroussi | |
| 5,928,527 A * | 7/1999 | Li et al. | 216/67 |
| 5,939,829 A | 8/1999 | Schoenbach et al. | |
| 6,005,349 A | 12/1999 | Kunhardt et al. | |
| 6,007,742 A | 12/1999 | Czernichowski et al. | |
| 6,016,027 A | 1/2000 | De Temple et al. | |
| 6,027,616 A | 2/2000 | Babko-Malyi | 204/164 |
| 6,096,564 A * | 8/2000 | Denes et al. | 438/1 |
| 6,113,851 A | 9/2000 | Soloshenko et al. | |
| 6,118,218 A * | 9/2000 | Yializis et al. | 315/111.21 |
| 6,146,724 A | 11/2000 | Roth | |
| 6,147,452 A | 11/2000 | Kunhardt et al. | 313/582 |
| 6,170,668 B1 | 1/2001 | Babko-Malyi | 209/127.1 |
| 6,228,330 B1 | 5/2001 | Herrmann et al. | |
| 6,232,723 B1 | 5/2001 | Alexeff | |
| 6,245,126 B1 | 6/2001 | Feldman et al. | 95/59 |
| 6,245,132 B1 | 6/2001 | Feldman et al. | 96/28 |
| 6,255,777 B1 | 7/2001 | Kim et al. | |
| 6,322,757 B1 | 11/2001 | Cohn et al. | 422/186.04 |
| 6,325,972 B1 | 12/2001 | Jacobs et al. | |
| 6,333,002 B1 | 12/2001 | Jacobs et al. | |
| 6,365,102 B1 | 4/2002 | Wu et al. | |
| 6,365,112 B1 | 4/2002 | Babko-Malyi et al. | |
| 6,372,192 B1 | 4/2002 | Paulauskas et al. | 423/447.1 |
| 6,375,832 B1 | 4/2002 | Eliasson et al. | 208/141 |
| 6,383,345 B1 | 5/2002 | Kim et al. | |
| 6,395,197 B1 | 5/2002 | Detering et al. | 252/373 |
| 6,399,159 B1 | 6/2002 | Grace et al. | 427/536 |
| 6,433,480 B1 | 8/2002 | Stark et al. | |
| 6,451,254 B1 | 9/2002 | Wang et al. | |
| 6,458,321 B1 | 10/2002 | Platt, Jr. et al. | |
| 6,475,049 B2 | 11/2002 | Kim et al. | |
| 6,497,839 B1 | 12/2002 | Kasegawa et al. | |
| 6,509,689 B1 | 1/2003 | Kim et al. | |
| 6,545,411 B1 | 4/2003 | Kim et al. | |
| 6,548,957 B1 | 4/2003 | Kim et al. | |
| 6,570,172 B2 | 5/2003 | Kim et al. | |
| 6,580,217 B2 | 6/2003 | Kim et al. | |
| 6,589,481 B1 | 7/2003 | Lin et al. | |
| 6,599,471 B2 | 7/2003 | Jacobs et al. | |
| 6,627,150 B1 | 9/2003 | Wang et al. | |
| 6,632,323 B2 | 10/2003 | Kim et al. | |
| 6,635,153 B1 | 10/2003 | Whitehead | |
| 6,673,522 B2 | 1/2004 | Kim et al. | |
| 6,685,523 B2 | 2/2004 | Kim et al. | |
| 6,818,193 B2 | 11/2004 | Christodoulatos et al. | |
| 2001/0031234 A1 | 10/2001 | Christodoulatos et al. | |
| 2002/0011203 A1 | 1/2002 | Kim | |
| 2002/0011770 A1 | 1/2002 | Kim et al. | |
| 2002/0045396 A1 | 4/2002 | Kim | |
| 2002/0092616 A1 | 7/2002 | Kim | |
| 2002/0105259 A1 | 8/2002 | Kim | |
| 2002/0105262 A1 | 8/2002 | Kim | |
| 2002/0122896 A1 | 9/2002 | Kim et al. | |
| 2002/0124947 A1 | 9/2002 | Kim | |
| 2002/0126068 A1 | 9/2002 | Kim et al. | |
| 2002/0127942 A1 | 9/2002 | Kim et al. | |
| 2002/0139659 A1 | 10/2002 | Yu et al. | |
| 2002/0144903 A1 | 10/2002 | Kim et al. | |
| 2002/0148816 A1 | 10/2002 | Jung et al. | |
| 2002/0187066 A1 | 12/2002 | Yu et al. | |
| 2003/0003767 A1 | 1/2003 | Kim et al. | |
| 2003/0015505 A1 | 1/2003 | Yu et al. | |
| 2003/0035754 A1 | 2/2003 | Sias et al. | |
| 2003/0048240 A1 | 3/2003 | Shin et al. | |
| 2003/0048241 A1 | 3/2003 | Shin et al. | |
| 2003/0062837 A1 | 4/2003 | Shin et al. | |
| 2003/0070760 A1 | 4/2003 | Kim et al. | |
| 2003/0071571 A1 | 4/2003 | Yu et al. | |
| 2003/0085656 A1 | 5/2003 | Kunhardt et al. | |
| 2003/0127984 A1 | 7/2003 | Kim et al. | |
| 2003/0134506 A1 | 7/2003 | Kim et al. | |
| 2003/0141187 A1 | 7/2003 | Sohn et al. | |
| 2004/0022673 A1 | 2/2004 | Protic | |
| 2004/0184972 A1 | 9/2004 | Kelly et al. | |

FOREIGN PATENT DOCUMENTS

| | | |
|---|---|---|
| EP | 1 378 253 A1 | 1/2004 |
| WO | WO-00/67805 | 11/2000 |
| WO | WO-01/44790 A1 | 6/2001 |
| WO | WO-02/49767 A1 | 6/2002 |
| WO | WO-03/028880 A1 | 4/2003 |

OTHER PUBLICATIONS

Kunhardt, E.E., "Generation of Large-Volume, Atmosphereic-Pressure, Nonequilibrium Plasmas", *IEEE Transactions on Plasma Science*, vol. 28 No. 1, pp. 189-200, Feb. 2000.

Penetrante et al., "Non-Thermal Plasma Techniques for Abatement of Violatile Organic Compounds and Nitrogen Oxides", *INP Report XII*, pp. 18-46 (1996).

Chen D.C.C., Lawton, J., and Weinberg, F.K., *Tenth Symposium on Combustion*, pp. 743-754 (1965).

Tarnovsky, V. and Becker, K., *Plasma Sources Science and Technology*, vol. 4, No. 307 (1995).

Knight, Henry de Boyne, the Arc Discharge; its application to power control, *London Chapman & Hall* (1960).

L.A. Rosenthal and D.A. Davis, "Electrical Characterization of a Corona Discharge for Surface Treatment", *IEEE Transaction on Industry Applications*, vol. 1A-11, No. 3, pp. 328-335 (May/Jun. 1995).

S. Han, Y. Lee, H. Kim, J. Lee, J. Yoon, and G. Kim, "Polymer Surface Modification by Plasma Source Ion Implantation", *Surfaces and Coating Technology*, vol. 93, pp. 261-263 (1997).

Kolman et al., "Genotoxic effects of ethylene oxide, propylene oxide and epichlorohydrin in humans: update review" (1990-2000), Mutation Research 512 (2002) 173-194.

Schoenbach et al., "Special Issue on Nonthermal Medical/Biological Treatments Using Electromagnetic Fields and Ionized Gasses", IEEE Transactions on Plasma Science, vol. 28, No. 1, Feb. 2000.

Jacobs, "STERRAD 100S" Sterilization System; Advanced Sterilization products a Johnson & Johnson Company, 1999 Advanced Sterilization Products.

Sharpless et al. "Interaction of Organophosphonates with $O(^3P)$, $N(^4S)$, $)2(a^1\ g)$, and $O_3$", Non-Thermal Plasma Techniques of Pollution control, Nato ASI Series, vol. G 34,Part A, p. 123-137 (1993).

Paur, "Removal of Volatile Hydrocarbons From Industrial Off-Gas", Non-Thermal Plasma Techniques for Pollution Control, Nato ASI Series, vol. G34 Part B, p. 77-89 (1993).

Mizuno et al. "Application of Corona Technology in the Reduction of Greenhouse gases and Other Gaseous Pollutants", Non-Thermal Plasma Techniques for Pollution Control, Nato ASI Series vol. G34 Part B. 165-185 (1993).

Yamamoto et al., "Decomposition of Volatile Organic Compounds By a Packed-Bed Reactor and a Pulsed-Corona Plasma Reactor", Non-Thermal Plasma Techniques for Pollution Control, Nato ASI Series, vol. G34, Part B, p. 223-237 (1993).

Rosocha et al., Treatment of Hazardous Organic Wastes Using Silent Discharge Plasmas, Non-Thermal Plasma Techniques for Pollution Control, Nato ASI Series vol. G34 Part B, p. 281-308 (1993).

Patent Abstracts of Japan, JP 11 221489, Aug. 17, 1999, vol. 1999, No. 13, abstract, Fig. 1.

International Search Report for PCT/US02/35299 dated Sep. 25, 2003.

Babko-Malyi, Sergei and Nelson, Gordon L., "Experimental Evaluation of Capillary Korona Discharges", American Institute of Aeronautics and Astronautics, 30th Plasmadynamics and Lasers Conference: AIAA-99-3488 (Jun. 28-Jul. 1, 1999), pp. 1-14.

Stark, et al., "Direct Current Glow Discharges in Atmospheric Air", American Institute of Aeronautics and Astronautics, 30th Plasmadynamics and Lasers Conference: AIAA-99-3666 (Jun. 28-Jul. 1, 1999), pp. 1-5.

Babko-Mayli, Sergei, "Ion-drift Reactor Concept", Fuel Processing Technology (1999), pp. 231-246.

Broer, S., Th. Hammer, Romheld, M., "Treatment of Diesel-Engine Exhaust by Silent Discharge Plasma" INP Report XIII (1996).

Christ, Jr., Buckley, "Leak Testing of Tank Linings by High Voltage Discharge", ElectroTechnic Products, Inc. Guide for Using Company's Probes (1993).

Tarnovsky, V., et al., "Electron-impact ionization of atoms, molecules, ions and transient species", Plasma Sources Science and Technology, vol. 4, pp. 307-315 (1995).

Lawton, James, et al., Electrical Aspects of Combustion, Clarendon Press, Oxford (1969).

Han, S., et al., "Polymer Surface Modification by Plasma Source Ion Implantation", Surfaces & Coatings Technology, vol. 93, pp. 261-264 (1997).

Chen, D.C.C., et al., "Augmenting Flames with Electric Discharges", Tenth Symposium on Combustion, pp. 734-754 (1965).

Yamamoto, T., et al., "Decomposition of Volatile Organic Compounds by a Packed-Bed Reactor and a Pulsed-Corona Plasma Reactor", vol. B, pp. 223-237 of NATO ASI Series G, vol. 34, Penetrante, B.M. and Schultheis S.E., ed. (1992).

Kunhardt, E. E., "Generation of Large-Volume, Atmospheric-Pressure, Nonequilibrium Plasmas", IEEE Transactions on Plasma Science, vol. 28, No. 1, pp. 189-200, Feb. 2000.

Schoenbach, Karl, et al., "Special Issue on Nonthermal Medical/Biological Treatments Using Electromagnetic Fields and Ionized Gases", IEEE Transactions on Plasma Science, vol. 28, No. 1, pp. 2-5 (Feb. 2000).

Sharpless, R.L., et al., "Interaction of Organophosphonates with O(3P), N(4S), OS(A1G), and O3", vol. A, p. 123-137 of NATO ASI Series G, vol. 34, Penetrante, B.M. and Schultheis S.E., ed. (1992).

Jacobs, Paul T., Sterrad 100S Sterilization System Advanced Sterilization Procucts literature, p. 1-17 (1999).

Mizuno, A., et al., "Application of Corona Technology in the Reduction of Greenhouse Gases and Other Gaseous Polluants", vol. B, pp. 165-185 of NATO ASI Series G, vol. 34, Penetrante, B.M. and Schultheis S.E., ed. (1992).

Kolman, Ada, et al., "Genotoxic effects of ethylene oxide, poroylene oxide and epichlorohydrin in humans: update review (1990-2001)", Mutation Research 512, pp. 173-194 (2002).

Rosenthal, L.A., et al., "Electrical Characterization of a Corona Discharge for Surface Treatment", IEEE Transaction on Industry Applications, vol. 1A-11, No. 3, pp. 328-335 (May/Jun. 1975).

Vidmar, R. J., "On the Use of Atmospheric Pressure Plasmas as Electromagnetic Reflectors and Absorbers", IEEE Transactions of Plasma Science, vol. 18, No. 4, Aug. 1990.

Penetrante et al., "Non-Thermal Plasma Techniques for Abatement of Volatile Organic Compoudns and Nitrogen Oxides", INP Report XIII, pp. 18-46 (1996).

Paur, H.R., "Removal of Volatile Hydrocarbons from Industrial Off-Gas", vol. B, pp. 77-89 of NATO ASI Series G, vol. 34, Penetrante, B.M. and Schultheis S.E., ed. (1992).

Rosocha, L.A., et al., "Treatment of Hazardous Organic Wasets Using Silent Discharge Plasmas", vol. B, pp. 281-308 of NATO ASI Series G, vol. 34, Penetrante, B.M. and Schultheis S.E., ed. (1992).

Becker, Kurt H., et al., "Collisional and radiative processes in high-pressure discharge plasmas", Physics of Plasmas, vol. 9, No. 5, pp. 2399-2404 (May 2002).

* cited by examiner

IN SITU STERILIZATION AND DECONTAMINATION SYSTEM USING A NON-THERMAL PLASMA DISCHARGE

CROSS-REFERENCE TO RELATED APPLICATIONS

This The present application (a) is a continuation-in-part of U.S. patent application Ser. No. 09/738,923, filed on Dec. 15, 2000 now U.S. Pat. No. 6,818,193, which claims the benefit of U.S. Provisional Application Nos. 60/171,198, filed on Dec. 15, 1999, and 60/171,324 filed on Dec. 21, 1999; and (b) claims the benefit of U.S. Provisional Application Nos. 60/336,866, filed on Nov. 2, 2001, and 60/336,868, filed on Nov. 2, 2001. These applications are hereby incorporated by reference in their entirety. In addition, the present application claims the benefit of U.S. Provisional Application No. 60/369,654, filed on Apr. 2, 2002.

BACKGROUND OF THE INVENTION

1. Field of the Invention

The present invention is directed to a method and system for sterilization of air streams and decontamination of objects/surfaces and, in particular, to such a method and system using a non-thermal plasma discharge device or generator.

2. Description of Related Art

Suspension media (e.g., filters, carbon beds, electrostatic precipitators) used in air handling equipment for ventilation purposes capture various airborne contaminants, including but not limited to spores, viruses, biological material, particulate matter and bacteria. Over a period of use, undesirable contaminants become trapped and collect in the suspension media thereby degrading its performance and becoming a concentrated source of bio-hazards for a ventilation system. Heretofore, two conventional methods were employed to remove the contaminants from the suspension media, namely, replacing the suspension media or in situ periodic cleaning of contaminated material from the suspension media. Either of these conventional methods for disposal of the contaminants involve a high potential that some of the captured spores, pathogens, and other undesirable particulate matter may be released into the atmosphere. In addition, in the case in which the suspension media containing the undesirable particulate matter is to be replaced, the contaminated suspension media must be properly disposed. This is particularly important in hazardous areas such as hospitals, laboratories, operating rooms that are exposed to extremely hazardous pathogens (e.g., tuberculosis, small pox, anthrax) or other contaminants in which minimal concentrations can generate considerable deleterious health consequences if released through a ventilation system.

It is desirable to develop an apparatus and method for in situ decontamination of a suspension media that eliminates or substantially reduces release of contaminants into the ventilation system.

SUMMARY OF THE INVENTION

The present inventive process and system for sterilization and decontamination in accordance with the present invention enhances sterilization efficiency while reducing health and environmental hazards by employing biologically active yet relatively short living sterilizing species produced as a byproduct during the generation of non-thermal plasma, preferably in the presence of organics and oxygen.

Specifically, the present invention is directed to a method of sterilization of fluids and decontamination of objects such as suspension media, food products, ventilation ducts and medical instruments. Active sterilizing species of living byproducts of non-thermal plasma-chemical reactions having a relatively short life (e.g., milliseconds or seconds) are generated. Due to the relatively short lifetime of the active sterilizing species their sterilization capabilities are greatest while in the vicinity of the non-thermal plasma discharge device. At the same time, due to its short lifetime the active sterilization species decompose rapidly into benign non-hazardous byproducts. This decomposition characteristic is particularly useful in situations where sterilization must be realized with minimal health and environmental hazards. To further enhance the sterilization efficiency rate an additive, carrier or free fluid such as various organic compounds (typically air) may be injected through the electrodes (or directly) into the plasma discharge apparatus. The introduction of an additive, carrier or free liquid into the plasma discharge apparatus increases production of active sterilizing species that are carried with the fluid flow and thus is able to be directed, as desired, to particular regions or areas of an object to be sterilized or decontaminated.

By way of example, in the case of air treatment, an air filter is installed downstream of the non-thermal plasma discharge device. Contaminated air to be treated is passed first through the non-thermal plasma discharge device and then through a filter. Some spores and bacteria are captured on the filter while others have already been inactivated upstream by direct interaction with active sterilizing species generated by the non-thermal plasma discharge device. The filter may be continuously or periodically exposed to the active sterilizing species generated upstream in order to significantly if not totally deactivate pathogens captured downstream on the filter. At the same time, active sterilizing species are decomposed within or downstream of the filter so that air expelled or passing through the filter into the room contains de minimis, if any, sterilizing agent. Additional filtration and catalyst media (e.g., ozone catalyst) may be added downstream to further reduce any remaining traces of undesirable contaminants and/or byproducts from the airflow.

Circulation of a carrier gas (typically air) advantageously provides efficient transport of the active sterilizing species to the desired contaminated regions or areas of the suspension media to be treated. As soon as power to the plasma discharge device is turned off, the active sterilizing species ceases to be generated and the objects may be immediately removed from the chamber without further delay.

In one preferred embodiment, the plasma generating system has a dielectric capillary or dielectric slit configuration capable of producing non-thermal plasma gas discharge in ambient air or other gas by applying RF, DC or AC high voltage to the electrodes. The byproducts of the plasma-chemical reactions (such as ozone, nitrogen oxides, organic acids, aldehydes) that are always present in the discharge afterglows in trace amounts are captured in the off-gas treatment system based on adsorption, catalysis or other processes typically used for removal of these byproducts from air.

Employment of ethanol/air or other organic vapor/air mixture as an additive, carrier or free fluid to be passed through the electrode into the discharge zone increases the generation of active sterilizing species that deactivate pathogens by promoting the replacement of a hydrogen atom in bacterial DNAs by an alkyl group ($C_nH_{2n+1}$). Alkylation is believed to be one mechanism by which ethylene oxide (one of the common sterilizing agents) deactivates pathogens. It is likely that alkylation is a primary mechanism of sterilization in the oxygen/organic plasma afterglow.

One embodiment of the present invention is directed to a sterilization and decontamination system including a plasma discharge device, preferably a non-thermal plasma discharge device, having a primary dielectric with at least one aperture defined therethrough that allows the passage of the plasma discharge. The system further includes a suspension media disposed downstream of the plasma discharge device. In addition, the invention relates to a method of sterilization and decontamination using the system described above. Plasma generated active sterilizing species is produced by applying a voltage differential to the primary electrode and receiving electrode to emit a plasma discharge through the at least one aperture. The contaminated fluid to be treated is then exposed to the generated active sterilizing species. Particulate matter is collected from the exposed fluid to be treated in the suspension media. Thereafter, some or all of the collected particulate matter is cleansed from the filter by exposing, spraying or bombardment of the filter with the generated active sterilizing species.

BRIEF DESCRIPTION OF THE DRAWING

FIG. 2b is an exemplary single representative pin segmented electrode and associated capillary in the capillary dielectric configuration plasma discharge device of FIG. 2a;

FIG. 3b is an exemplary slit dielectric R13 rod configuration plasma discharge device of FIG. 3a;

FIG. 5*a* is a bottom view of an exemplary non-thermal plasma sterilization and decontamination system in the accordance with the present invention that is displaceable in at least one direction; and

FIG. 5*b* is a side view of the sterilization and decontamination system of FIG. 5*a*.

DETAILED DESCRIPTION OF THE INVENTION

The method described utilizes organic vapors (by way of example, alcohols) in a non-thermal plasma discharge to accelerate and improve overall sterilization rates on surfaces and in air streams. This can be applied to a variety of thermal and non-thermal plasma reactor devices. These reactors can operate using DC, AC or RF power supplies, and with a continuous or periodic supply of power.

The segmented electrode capillary discharge, non-thermal plasma reactor in accordance with the present invention is designed so that a solid or a fluid (e.g., a liquid, vapor, gas or any combination thereof) to be treated containing undesirable chemical agents, for example, an atomic element or a compound, is exposed to a relatively high density plasma in which various processes, such as oxidation, reduction, ion induced composition, and/or electron induced composition, efficiently allow for chemical reactions to take place. The ability to vary the energy density allows for tailored chemical reactions to take place by using enough energy to effectively initiate or promote desired chemical reactions without heating up the bulk gas. By way of example, the present invention will be described with respect to the application of using the plasma reactor to purify or sterilize contaminated objects or fluid streams. It is, however, within the intended scope of the invention to use this method and associated devices for other applications.

The dimensions of the reaction chamber may be selected, as desired, such that the residence time of the pollutants within the plasma regions is sufficient to ensure destruction of the contaminant to a desired level, for example, deactivation of the contaminants down to the molecular level. Furthermore, in the case in which a carrier, additive or free fluid is injected into the plasma discharge device, the rate of injection and location of injection of the additive fluid may be varied, as desired, to deliver the additive fluid through the region where the plasma originates (e.g., the capillary or slit) or through an auxiliary feed port that intersects with the aperture in which the plasma discharge is emitted. Additionally, the reactor may be sized to such residence time, that the pollutants and biological contaminants may be deactivated, but not destroyed, effectively sterilizing the treated surface, media or fluid. In addition, desired chemical reactions may be achieved by employing an additive, free or carrier fluid so that the radicals formed exist beyond the plasma region for a duration sufficient to effect a sterilization or oxidative process.

FIG. 1 is an exemplary schematic flow diagram of the plasma sterilization and decontamination system in accordance with the present invention. A source of contaminated fluid 155, e.g., a liquid and/or a gas, to be treated may contain pathogens (e.g., viruses, spores) and/or undesirable chemical compounds (e.g., benzene, toluene). The contaminated fluid 155 passes through a decontamination or sterilization device 165 that includes a non-thermal plasma discharge device 105 and a suspension media 115. Non-thermal plasma discharge device 105 may be one of many different configurations, for example, a corona discharge, a barrier discharge, a capillary dielectric discharge (U.S. patent application Ser. No. 09/738,923, filed Dec. 15, 2000) or a slit dielectric discharge (U.S. patent application Ser. No. 10/287,772, entitled "Non-Thermal Plasma Slit Discharge Apparatus", filed on Nov. 4, 2002, which claims priority to U.S. Provisional Application Ser. No. 60/336,866, filed on Nov. 2, 2001). Although the use of a non-thermal plasma discharge device is preferred, a thermal plasma discharge device may be employed but will yield a less efficient rate of sterilization. Energy is supplied to the non-thermal plasma discharge device 105 by a high voltage power supply, for example, a direct current, alternating current, high frequency, radio frequency, microwave, pulsed power supply, depending on the desired plasma discharge configuration. While passing through the non-thermal plasma discharge device 105 the contaminated fluid 155 is exposed to the plasma as well as to the active sterilizing species such as organic radicals and/or ion clusters created as a byproduct during the generation of the plasma. Exposure of the contaminated fluid to the plasma generated active sterilizing species substantially deactivates the pathogens and reduces concentrations of undesirable chemicals into more benign compounds.

Four reaction mechanisms that contribute to the plasma enhanced chemistry responsible for formation of the active sterilizing species will now be described. Common to all four reaction mechanisms is that of electron impact dissociation and ionization to form reactive radicals. The four reaction mechanisms include:

(1) Oxidation: e.g., conversion of $CH_4$ to $CO_2$ and $H_2O$ $$e^- + O_2 \rightarrow e^- + O(3P) + O(1D)$$

$$O(3P) + CH_4 \rightarrow CH_3 + OH$$

$$CH_3 + OH \rightarrow CH_2 + H_2O$$

$$CH_2 + O_2 \rightarrow H_2O + CO$$

$$CO + O \rightarrow CO_2$$

(2) Reduction: e.g., reduction of NO into $N_2 + O$ $$e^- + N_2 \rightarrow e^- + N + N$$

$$N + NO \rightarrow N_2 + O$$

(3) Electron induced decomposition: e.g., electron attachment to $CCl_4$ $$e^- + CCl_4 \rightarrow CCl_3 + Cl^-$$

$$CCl_3 + OH \rightarrow CO + Cl_2 + HCl$$

(4) Ion induced decomposition: e.g., decomposition of methanol $$e^- + N_2 \rightarrow 2e^- + N_2^+$$

$$N_2^+ + CH_3OH \rightarrow CH_3^+ + OH + N_2$$

$$CH_3^+ + OH \rightarrow CH_2^+ + H_2O$$

$$CH_2^+ + O_2 \rightarrow H_2O + CO^+$$

Figure 1:
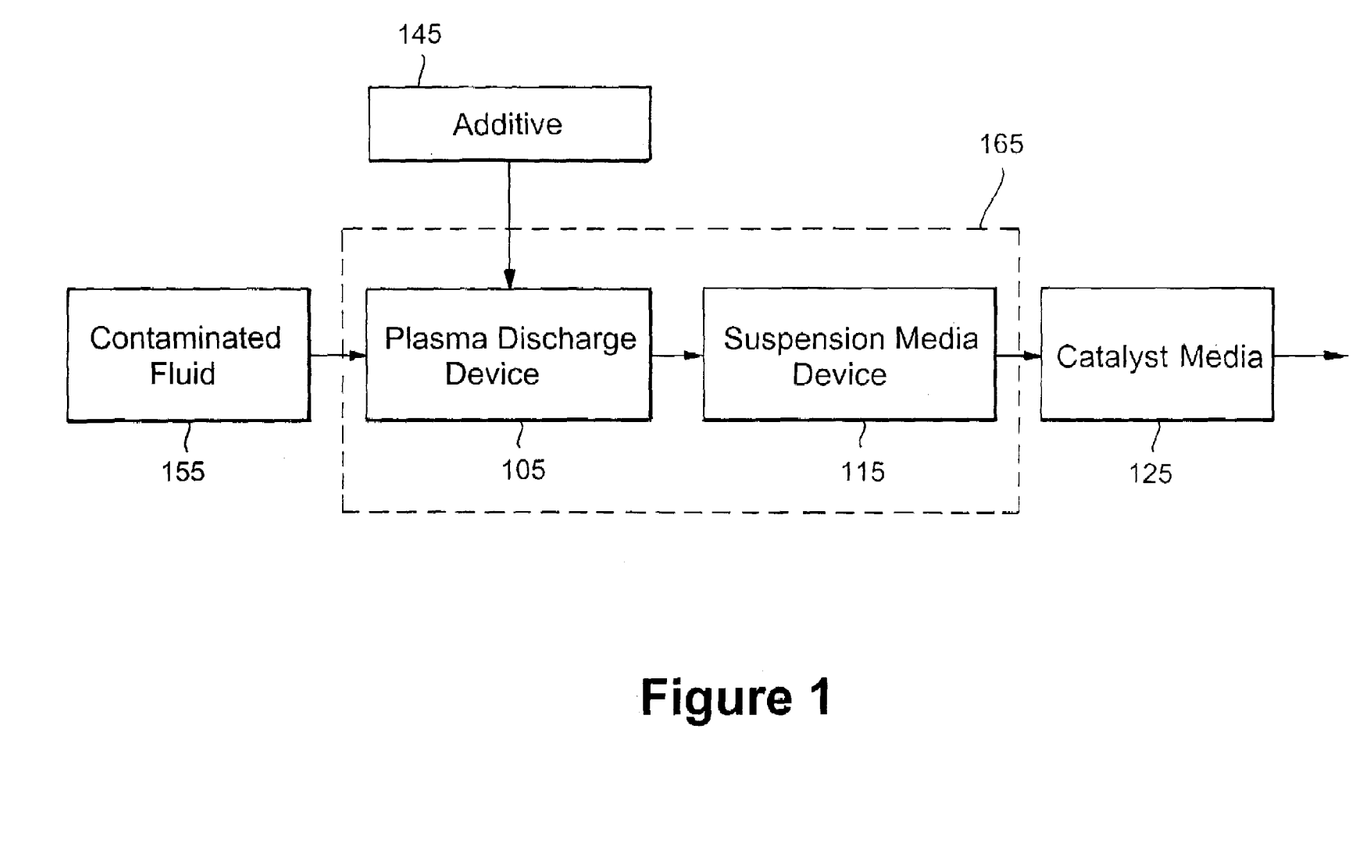
FIG. 1 is a schematic overview of a non-thermal plasma sterilization and decontamination system in accordance with the present invention.

In a preferred embodiment, an additive, free or carrier fluid 145, e.g., an alcohol such as ethanol or methanol, may be injected into the non-thermal plasma discharge device 105 to enhance the sterilization effect or overall plasma chemistry. Specifically, the additive, free or carrier fluid increases the concentration of plasma generated active sterilizing species while reducing the generation of undesirable byproducts (e.g., ozone pollutants). Accordingly, employing an additive, free or carrier fluid can advantageously be used to tailor the chemistry of the plasma generated active sterilizing species.

When organic/air mixtures are used as an additive, feed or carrier gas, the following chemical reaction chains are instrumental in the generation of additional active sterilizing species. Illustrative examples are provided with respect to each chemical reaction chain.

1) Formation of ions and ion clusters:

$$e + N_2 \rightarrow N_2^+ + 2e \quad e + O_2 \rightarrow O_2^+ + 2e$$

$$N_2^+ + N_2 \rightarrow N_4^+ \quad O_2^+ + O_2 \rightarrow O_4^+$$

$$N_4^+, N_2^+ + O_2 \rightarrow O_2^+ + \text{products}$$

$$O_2^+, O_n^+ + H_2O \rightarrow O_2^+(H_2O)$$

$$O_2^+(H_2O) + H_2O \rightarrow O_2^+(H_2O)_2 \rightarrow H_3O^+(OH) + O_2$$

$$H_3O^+(OH) + H_2O \rightarrow H_3O^+(H_2O) + OH$$

$$H_3O^+(H_2O) + nH_2O \rightarrow H_3O^+(H_2O)_2 + (n-1)H_2O \rightarrow H_3O^+(H_2O)_n + (n-h)H_2O$$

Hydronium ion clusters can protonate ethyl alcohol when present in the feed gas, as shown by the following illustrative example:

$$H_3O^+(H_2O)_h + EtOH \rightarrow EtOH_2^+(H_2O)_b + (h+1-b)H_2O$$

Ion clusters such as $EtOH_2^+(H_2O)_b$ increase sterilization efficiency as a result of their reasonably long life time. Accordingly, ion clusters are able to survive the transport to the targeted object to be sterilized and provide an Et group for replacement of a hydrogen atom in bacterial DNAs which will lead to deactivation of the targeted microorganisms. Organic ions, such as $C_2H_4OH^+$, $C_2H_3OH^+$, $CH_2OH^+$, $CHOH^+$, $CH_3OH^+$, $C_2H_5^+$ are also formed when an additive, free or carrier fluid is employed and may improve sterilization depending on their lifetime and chemical activity.

2) Formation of Free Radicals:

$$e^- + O_2 \rightarrow e^- + O + O(1D)$$

$$e^- + O_2 \rightarrow e^- + O_2^*$$

$$e^- + N_2 \rightarrow e^- + N + N, \quad N + O_2 \rightarrow NO + O$$

$$e^- + N_2 \rightarrow N_2^* + e^-, \quad N_2^* + O_2 \rightarrow N_2 + O + O$$

$$O + O_2 + M \rightarrow O_3 + M, \quad O_2^* + O_2 \rightarrow O_3 + O$$

$$O(1D) + H_2O \rightarrow 2OH$$

Other numerous chemical reactions leading to formation of $NO_2$, $HO_2$ and other active species, for example, $H_2O_2$, are possible.

In the presence of organics, formation of organic radicals will occur:

$$RH + OH \rightarrow R + H_2O, \quad R + O_2 + M \rightarrow RO_2 + M,$$

$$RO_2 + NO \rightarrow RO + NO_2, \quad RO + NO_2 + M \rightarrow RONO_2 + M,$$

$$RO + O_2 \rightarrow RCHO + HO_2,$$

Presence of organics and oxygen in plasma will also promote the formation of other organic radicals such as peroxy $RO_2$, alkoxy RO, acyl peroxyacyl $RC(O)OO$ and byproducts, such as hydroperoxides (ROOH), peroxynitrates ($RO_2NO_2$), organic nitrates ($RONO_2$), peroxyacids ($RC(O)OOH$), carboxylic acids ($RC(O)OH$) and peroxyacyl nitrates $RC(O)O_2NO_2$.

Referring once again to FIG. 1, the contaminated fluid 155 after being exposed to the generated plasma passes through a suspension media 115 (e.g., a filter, electrostatic precipitator, carbon bed or any other conventional device used to remove particulate material from fluid streams) disposed downstream of the plasma discharge device 105. Residual pathogens that have not been entirely neutralized or deactivated when exposed to the plasma discharge in the plasma discharge device are collected in the suspension media 115. These collected contaminants are treated upon contact with the suspension media 115 by the radicals and ions created by the generated plasma as part of the fluid stream. Compounds such as carbon beds and microorganisms that collect in the suspension media 115 have the beneficial effect of reacting with the plasma generated active sterilizing species upon contact with the suspension media. Specifically, organic byproducts and radicals along with other active species interact with the DNA and other building blocks of microorganisms deposited on the suspension media device 115. By way of example, replacement of a hydrogen atom in bacterial DNA by an alkyl group ($C_nH_{2n+1}$) due to exposure to the plasma generated active sterilizing species leads to inactivation of microorganisms. Alkylation is believed to be but one mechanism responsible for sterilization in the described method, other mechanisms and active sterilizing species may also be present.

Optionally, the plasma treated fluid may be exposed to a catalyst media 125 (e.g., an ozone catalyst) or additional suspension media disposed downstream of the suspension media 115 to further reduce concentrations of residual undesirable compounds such as ozone and/or pathogens.

Figure 2A:
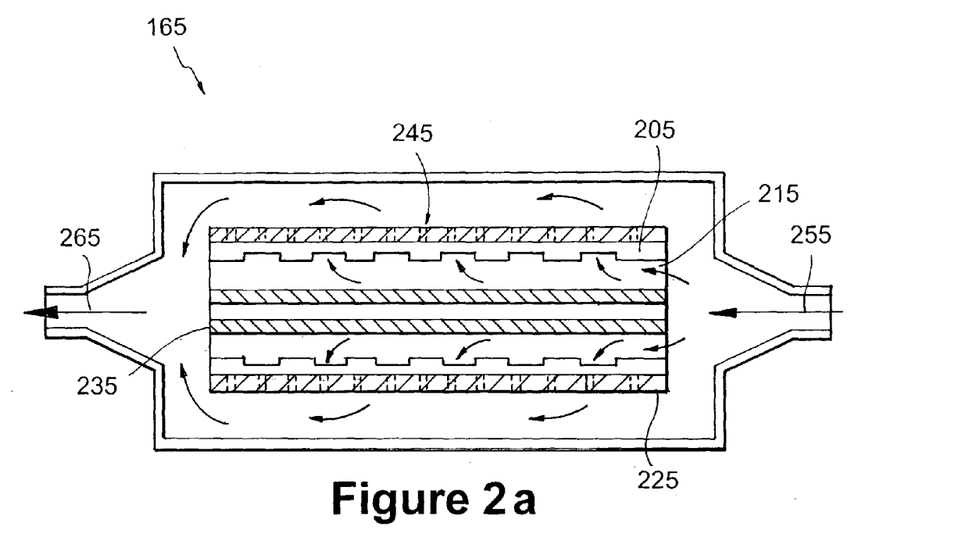
FIG. 2a is a longitudinal cross-sectional view of an exemplary non-thermal plasma sterilization and decontamination system having a capillary dielectric discharge configuration in accordance with the present invention.
Figure 2B:
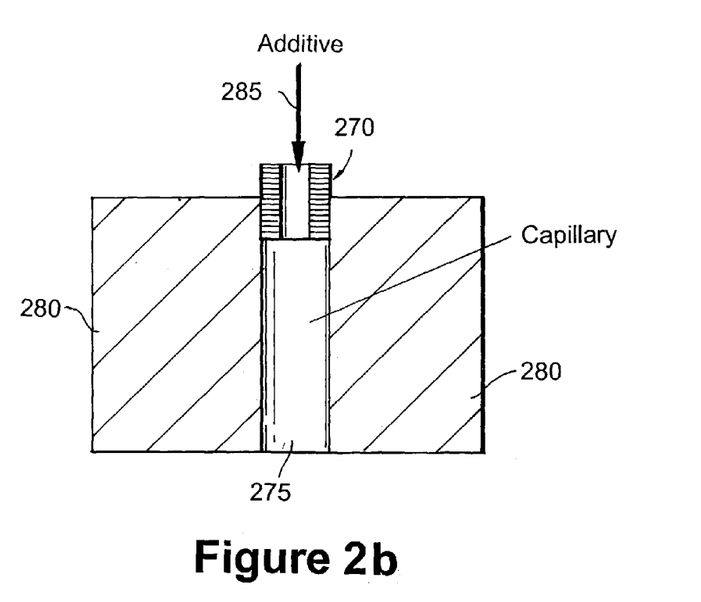

FIG. 2a is a longitudinal cross-sectional view of an exemplary first embodiment of the sterilization and decontamination unit 165 of FIG. 1 having a non-thermal plasma capillary dielectric segmented electrode discharge configuration 235 (as described in U.S. patent application Ser. No. 09/738,923, filed Dec. 15, 2000, which is herein incorporated by reference in its entirety) and a filter 245. This combination plasma-filter device simultaneously captures and destroys biological particulate matter such as spores and bacteria. Contaminated fluid to be treated is received through the inlet port 255 of the sterilization and decontamination unit 165. The capillary dielectric segment electrode 235 has a primary dielectric with at least on capillary defined therethrough and a segmented electrode containing a plurality of electrode segments disposed proximate and in fluid communication with respective capillaries. FIG. 2b is a partial cross-sectional view of an exemplary configuration of a single segmented electrode and an associated capillary of the capillary dielectric segmented electrode 235 shown in FIG. 2a. The electrode segment is in the shape of a blunt end pin 270 disposed proximate and partially inserted into the respective capillary 275 defined in the primary dielectric 280. An additive, carrier or free fluid 285 may be injected into the capillary either through the segmented pin electrode 270 if it is hollow (as shown in FIG. 2b) or alternatively if the segmented electrode is solid the additive may be injected through an auxiliary channel defined in the primary dielectric that intersects with the capillary 275. Numerous other configurations of the segmented electrode are contemplated as disclosed in U.S. patent application Ser. No. 09/738,923, for example, as a ring or washer disposed proximate the capillary.

Referring once again to FIG. 2a, the contaminated fluid to be treated passes through a plasma region or channel 225 disposed between the capillary dielectric segmented electrode 235 and a receiving electrode 205 having a plurality of holes or apertures defined therein to permit the passage of plasma discharge therethrough. A filter 245 is disposed between the receiving electrode 205 and a perforated support plate 225.

In operation, plasma is generated in the plasma region 215 upon the application of a voltage differential between the capillary dielectric segmented electrode 235 and receiving electrode 205. Contaminated fluid to be treated that is laden with undesirable particulate matter passes into and is exposed to the generated plasma active sterilizing species in the plasma region 215. The contaminated fluid after being exposed to the generated plasma passes through the filter 245 in which a substantial amount of the undesirable particulate matter is collected. Filter 245 is subject to continuous or periodic bombardment, spraying or exposure to plasma discharge from the capillary dielectric segmented electrode 235. Plasma generated active sterilizing species upon contacting with the filter 245 further deactivate the collected undesirable particulate matter and the treated fluid passes through the perforations in the support plate 205 and out from the outlet port 265 of the sterilization and decontamination unit 165. The capillary dielectric segmented electrode configuration 235 provides relatively large residence times of the spores on the surface of the filter ensuring a relatively high rate of decontamination without reducing the air flow rate.

Preferably, the filter 245 is a HEPA filter having a capture efficiency of approximately 99.97% down to a particle size of approximately 0.3 microns. Anthrax spores have a diameter approximately 3 micron. Weaponized anthrax particulates are only of the order of 1–3 microns. Thus, either type of anthrax spore may be captured using a HEPA filter and then decontaminated by the organic vapor plasma chemistry in accordance with the present invention. To further enhance the sterilization efficiency in accordance with the present invention, the contaminated filter or other suspension media is exposed or subject to bombardment of plasma generated active sterilizing species in the presence of an additive, carrier or free gas, such as organic or water vapors.

Figure 3A:
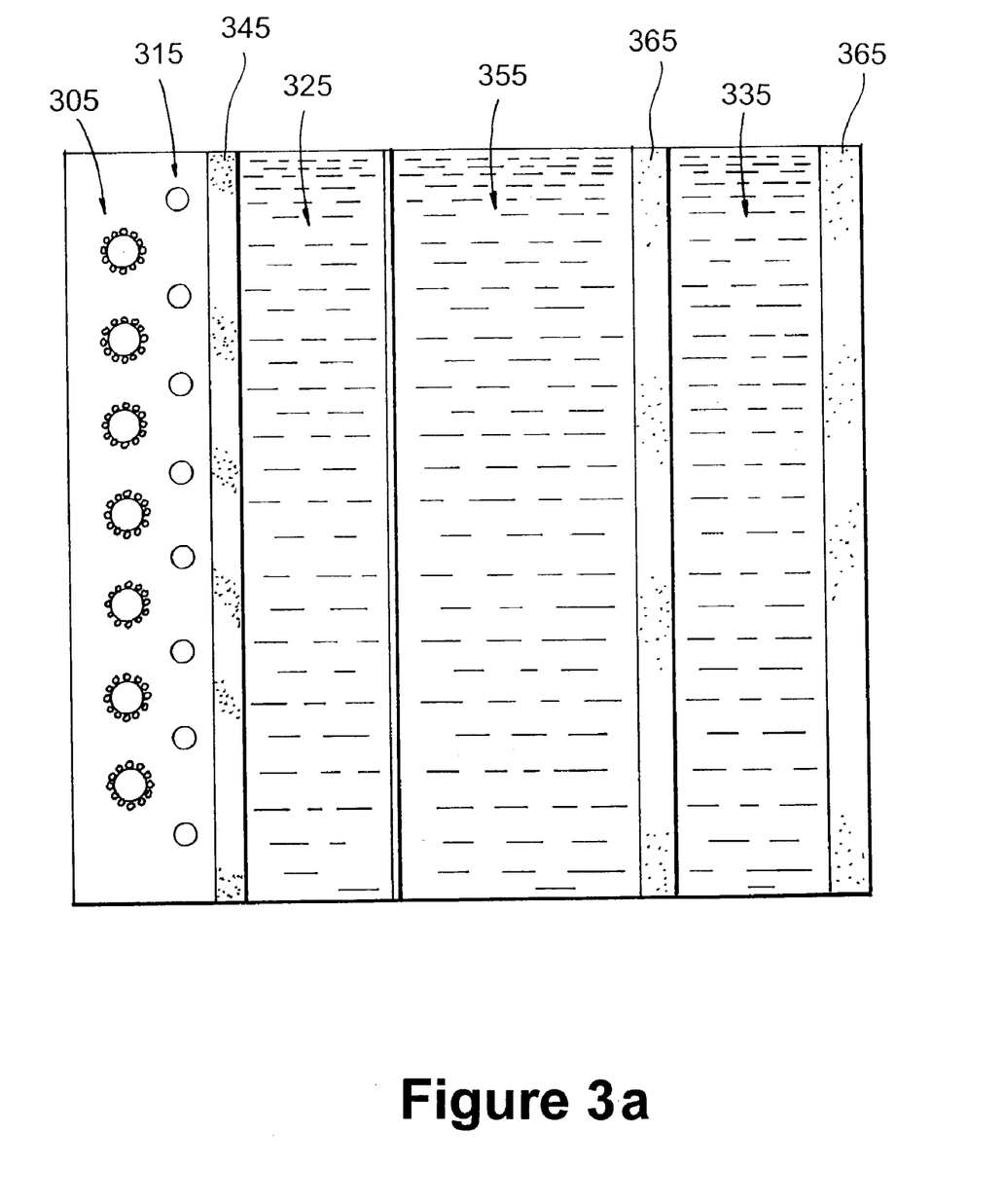
FIG. 3a is an exemplary cross-sectional view of a non-thermal plasma sterilization and decontamination system having a non-thermal plasma slit dielectric discharge configuration in accordance with the present invention.
Figure 3B:
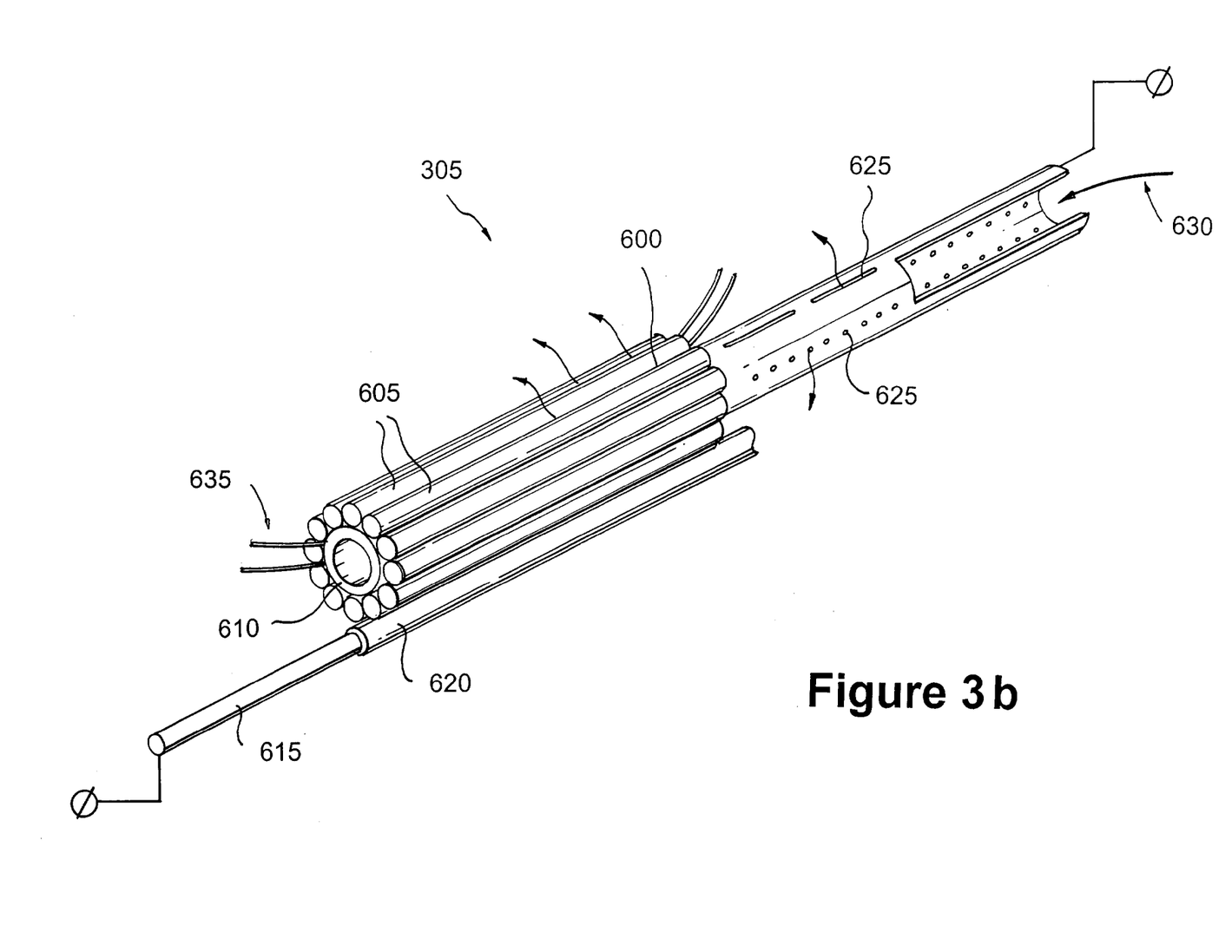

FIG. 2 shows a non-thermal plasma sterilization and decontamination using having a capillary dielectric configuration. FIG. 3a shows an alternative exemplary plasma sterilization and decontamination system having a slit dielectric discharge configuration, as described in the non-provisional U.S. patent application Ser. No. 10/287,772, entitled "Non-Thermal Plasma Slit Discharge Apparatus", filed on Nov. 4, 2002, which claims priority to U.S. Provisional Patent Application Ser. No. 60/336,866, filed on No. 2, 2001, each of which are herein incorporated by reference in their entirety. Additives to enhance plasma chemistry (in this case organic vapors) are delivered or injected through the slit dielectric discharge electrode 305 and the resulting plasma chemistry is formed in the plasma region created between the slit dielectric discharge electrode 305 and a grounding or receiving electrode 315. By way of example, the slit discharge electrode has thirteen dielectric rods 605 as shown in FIG. 3b, however, other electrode configurations may be used as desired. Adjoining dielectric rods 605 are disposed about an inner central cylinder 610 (made from a conductive or dielectric material) and separated from one another to form an open ended slit 600 therebetween. Preferably, the inner central cylinder 610 is hollow and has perforations 625 (e.g., holes and/or slots) about its perimeter. An additive, carrier or free fluid 630 may be injected through the hollow center of the cylinder 610 and pass through the perforations 625 in its perimeter. This additive 630 then mixes with plasma generated in the slits 600 defined between the adjacent dielectric rods 605 upon the application of a voltage differential between the inner central cylinder 610 and a receiving electrode 615 (encased in a secondary dielectric sleeve 620).

Referring back to FIG. 3a, plasma generated active sterilizing species include radicals that are carried forth and chemically react with those biological agents collected in the suspension media 325 downstream of the plasma discharge device. An ozone or other catalyst media 335 is preferably employed to further reduce any residual ozone plasma generated active sterilizing species. A carbon filter 345 may be used to further eliminate any residual smells or odors not remediated in the plasma region. Additional filters 355, 365 may be added if desired for further particulate removal from the fluid stream being treated.

Figure 4:
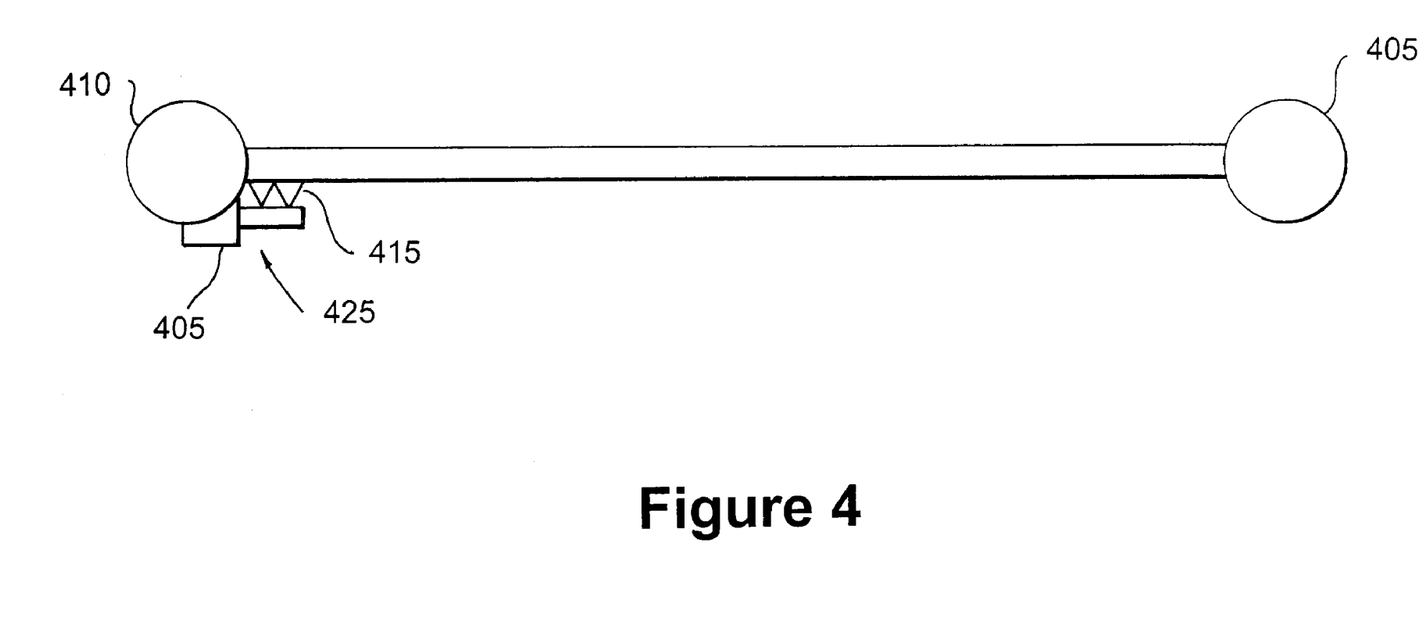
FIG. 4 details a system whereby the suspension media is wound and travels along a path along which it is exposed to non-thermal plasma generated by a non-thermal plasma discharge device whereafter the treated suspension media is wound up about a receiving roller;

Yet another embodiment of the in situ plasma sterilization and decontamination system in accordance with the present invention is shown in FIG. 4. The system in accordance with this embodiment is somewhat analogous to a conventional paper roller or conveyor belt system. A supply drum 405 upon which the suspension media 425 to be treated is wound is disposed at one end while a receiving drum 410 is disposed at an opposite end about which the suspension media 425 traveling in the direction indicated by the arrow after it has been treated, bombarded or exposed to the plasma 415 produced by the non-thermal plasma sterilization and decontamination unit 105 is wound. The plasma sterilization and decontamination unit 105 may be any type of configuration such as a corona discharge, barrier discharge, capillary discharge or slit discharge configuration.

Figure 5A:
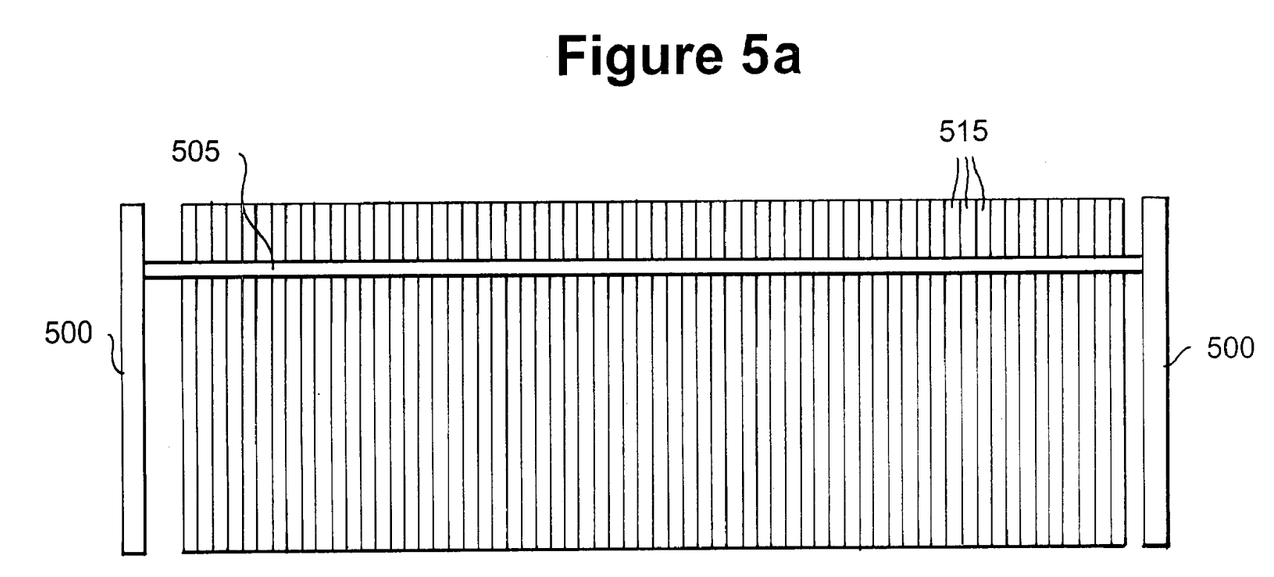
Figure 5B:
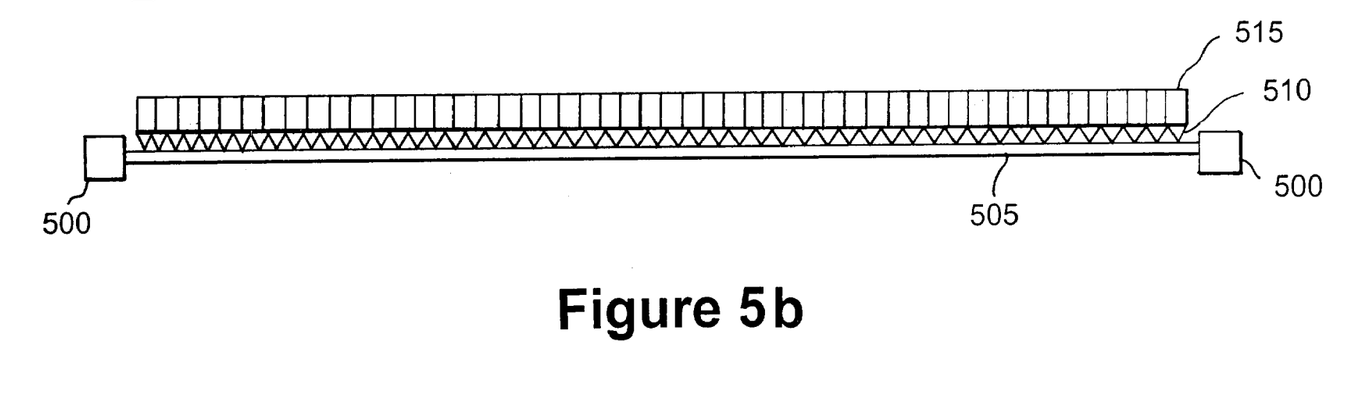

Another embodiment of the non-thermal plasma sterilization and decontamination system in accordance with the present invention is shown in FIGS. 5a and 5b. In this alternative sterilization and decontamination system an in situ sterilization and decontamination unit 505 is movable or displaceable in at least one direction along a rack. By way of example, the non-thermal plasma sterilization and decontamination unit 505 shown in FIGS. 5a and 5b is a slit dielectric discharge configuration displaceable along parallel supports 500 in a single direction indicated by the arrows. It is, however, contemplated and within the intended scope of the present invention to use a corona discharge, barrier discharge, or capillary dielectric discharge configuration plasma sterilization and decontamination unit 505. Furthermore, the non-thermal plasma sterilization and decontamination unit 505 may be displaceable in any desired direction or more than one direction. Alternatively, the non-thermal plasma sterilization and decontamination unit 505 may remain stationary while the array of suspension media 515 to be treated is displaced accordingly until its entire surface has been exposed or treated by the plasma 510 emitted from the non-thermal plasma sterilization and decontamination unit 505. A single non-thermal plasma sterilization and decontamination unit 505 is shown in FIGS. 5a and 5b, however, any number of one or more units may be used as desired to treat the filter array.

Active sterilizing species based on O, H and N atoms ($NO_2$, $H_2O_3$, and correspondent radicals such as $HO_2$, $OH$) as employed with conventional methods and apparatus are significantly less effective sterilizers than the byproducts, radicals and ions of organic/air plasma, as in the present invention. It should be noted that the addition of an additive, free or carrier fluid such as an organic compound into the plasma will not significantly change the nature of the plasma generated active sterilizing species but do substantially increase the concentration and relative amounts of these species. One significant distinguishing property of the described present inventive sterilization method over that of conventional apparatus is the presence of both organics and oxygen (air) in the gas-discharge plasma. Heretofore, conventional sterilization methods relied on O/H/N based species or on direct effects of electric fields, plasma or radiation, while the present inventive sterilization method relies on organic based active species formed in the gas-discharge plasma.

Experiments to establish the effectiveness of the present inventive method and apparatus were performed using standard biological spore strips of *Bacillus Subtilis* obtained from Raven Laboratories. Testing was conducted using a dielectric capillary segmented electrode with a plurality of primary wire electrodes inserted in respective capillaries (0.53 mm ID) defined in a quartz dielectric and the receiving copper wire electrodes encased in a quartz tubing (3 mm OD, 1.8 mm ID) with the tips of the primary electrodes aligned at the level of the axes of receiving electrodes. The *Bacillus Subtilis* strips were placed in contact with the filter media to simulate an accumulation or collection of biological matter on the surface of the suspension media. Initial sterilization test on the filter were conducted using ambient (considered dry air) injection as an additive fluid. Later tests were conducted with various water vapor or alcohol additives to compare results for sterilization of the filter media with and without the presence of alcohol in the carrier fluid. Specifically, air was bubbled through water or methyl alcohol and passed through the capillaries of the plasma reactor spraying the plasma generated active sterilizing species onto the spore containing strips.

In the experiments conducted using ambient (considered dry) air injection as the additive it was found that the effect of non-thermal plasma treatment on spore deactivation became noticeable after approximately 5 min of treatment time (90% deactivation) with growth of spores occurring after 12 to 15 hours. Untreated control spores started to grow within the first 12 hours. In the other experiments with water or alcohol additives it was determined that the addition of methyl alcohol significantly increased the deactivation rates while suppressing the concentration of undesirable ozone pollutants.

Sterilization efficiency results of the capillary discharge segmented electrode configuration in accordance with the present invention using different additives (e.g., methanol, ethanol) to the carrier gas (ambient air) at a constant discharge power (50 kHz frequency) toward inactivation of *Bacillus Subtilis* spores incorporated into dry filtration paper is presented in the table below.

| Additives to a Carrier Gas (air) | No additives | Water Injection | Additive #1 (Methanol) Injection | Additive #2 (Ethanol) Injection |
| --- | --- | --- | --- | --- |
| Output generator power (wt) @ 50 kHz | 100 | 100 | 100 | 100 |
| Flow rate of the carrier gas through the capillaries (lpm) | 1 | 1 | 1 | 1 |
| Average concentration of ozone, ppmV | 200 | 150 | 15 | <15 |
| Inactivation efficiency at exposure time 2 min, % | <90 | — | 99.9 | 99.999 |
| Inactivation efficiency at exposure time 5 min, % | 99 | 90 | >99.9999 | >99.9999 |
| Inactivation efficiency at exposure time 10 min, % | 99.9 | 95 | | |
| Inactivation efficiency at exposure time 20 min, % | 99.99 | — | | |
| Inactivation efficiency at exposure time 40 min, % | >99.9999 | — | | |
| 4-log inactivation time, min | 20 | >20 | 3 | <2 |

From the results in the table above it is clear that a plasma reactor placed upstream of the filter generates sufficient radicals to sterilize the face of an air filter. The rate of sterilization associated with this process has been determined to be dependent on several variables. One such variable is the selection of plasma chemistry by the introduction as an additive, free or carrier gas into the primary dielectric dry air and/or other selected additives such as alcohols or water. The use of an additive, free or carrier fluid results in a faster rate of sterilization, however, inactivation of particulate matter at smaller concentrations may be realized without the use of an additive. Another variable that has an impact on the rate of sterilization is the power expended. That is, the greater the power applied to the produce the non-thermal plasma the higher the sterilization rate. The distance of separation between the emission of plasma from the plasma discharge device and that of the suspension media to be treated is yet another variable that influences the rate of sterilization of particulate matter.

Based on the experimental results it has been determined that the deactivation of spores did not correlate directly to the concentration of ozone (which is a strong sterilizing agent itself) in the plasma generated discharge off-gas, thereby inferring that the plasma-chemistry involves some active sterilizing species generated from organics that have been injected through the electrode into the plasma zone.

Additional experiments were conducted using a slit dielectric rod type (R13) discharge electrode design both with and without injection of ethyl alcohol/air mixture through the central tube. Concentrations of ozone and nitrogen oxides have been measured without airflow between the electrodes (natural convection). The results of these experiments are presented in a table below. Inactivation efficiency at a 60 Hz frequency system was high and injection of ethanol/air mixture as an additive significantly increased the sterilization rates.

| Additives to a Carrier Gas (air) | Position of the indicator (Distance from the injector electrode) | No additives | Additive #2 (Ethanol) Injection |
|---|---|---|---|
| Output generator power (wt) @ 60 Hz | | 35 | 35 |
| Applied voltage (p-p) 15 kV | | | |
| Flow rate of the carrier gas through the 13 rods electrode (lpm) | | | 1.5 |
| Average concentration of ozone, ppmV (natural convection) | 3 mm (between the electrodes) | 45 | 31 |
| Average concentration of nitrogen dioxide, ppmV (natural convection) | 3 mm (between the electrodes) | 53 | 53 |
| Inactivation efficiency at exposure time 2 min, % | 1 mm (between the electrodes) | 99 | >99.9999 |
| Inactivation efficiency at exposure time 5 min, % | 1 mm (between the electrodes) | 99.999 | |
| Inactivation efficiency at exposure time 10 min, % | 1 mm (between the electrodes) | >99.9999 | |
| Inactivation efficiency at exposure time 2 min, % | 16 mm | | >99.9999 |
| Inactivation efficiency at exposure time 10 min, % | 24 mm | | >99.9999 |
| Inactivation efficiency at exposure time 45 min, % | 150 mm | | >99.9999 |

When organic compounds in air carrier gas (or other oxygen containing gas) pass through the plasma discharge device various free radicals and other relatively long living (as compared to the life time of electrons and electronically excited species) active sterilizing species are generated. Some of these reaction products are hydroperoxides (ROOH), peroxynitrates ($RO_2NO_2$), organic nitrates ($RONO_2$), peroxyacids (RC(O)OOH), carboxylic acids (RC (O)OH), organic radicals such as peroxy $RO_2$—, alkoxy RO—, acyl peroxyacyl RC(O)OO—, and other active sterilizing species. Some of the oxygen-containing organics are known to be strong sterilizing agents (for example ethylene oxide). Placement of the filter downstream of the plasma discharge devices serves a dual purpose of deactivation of contaminated fluid as it passes through the plasma discharge region as well as cleaning the filter media by deactivation of the collected undesirable particulate matter when the plasma generated active sterilizing species contacts the filter. This is distinguished from prior art, which sterilize filters by placing the filter media sandwiched between the anode and cathode, as described in U.S. Pat. Nos. 6,245,132 and 6,245,126. Another advantageous feature of the present inventive arrangement it that the plasma discharge devices are operable both continuously as well as intermittently.

The plasma generated active sterilizing species in accordance with the present invention have stronger sterilizing agents than conventional sterilizing species generated on the base of oxygen, hydrogen and nitrogen—such as nitrogen dioxide, ozone, hydrogen peroxide and correspondent radicals and other byproducts (hydroxyl radicals etc.). At the same time, the plasma generated active sterilizing species are relatively short living so they decompose within the sterilization chamber or immediately after deactivating the particulate matter on the filter and thus pose less environmental and health hazards as conventional chemical sterilizing agents.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps which perform substantially the same function, in substantially the same way, to achieve the same results are within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

All of the references, publications and patents referred to herein are each incorporated by reference in their entirety.

What is claimed is:

1. A method of sterilizing or decontaminating an object using a plasma discharge device comprising the steps of:

introducing an additive fluid into the plasma discharge device, wherein the additive fluid is a mixture comprising an organic vapor and air;

producing a plasma generated active sterilizing species from the additive fluid;

emitting the plasma generated active sterilizing species from the plasma discharge device; and exposing the object to the emitted active sterilizing species downstream from the plasma discharge device.

2. The method in accordance with claim 1, wherein the plasma discharge device has a dielectric having at least one aperture defined therethrough and an electrode disposed proximate and in fluid communication with the at least one aperture, and the additive fluid is introduced into the plasma discharge device by injecting it into the aperture of the dielectric.

3. The method in accordance with claim 1, wherein the plasma discharge device has a capillary dielectric, slit dielectric, barrier discharge, or corona discharge configuration.

4. The method in accordance with claim 1, wherein the organic vapor comprise alcohol.

5. The method in accordance with claim 4, wherein the alcohol is ethanol or methanol.

6. The method in accordance with claim 1, wherein the object is a fluid, suspension media, food product, ventilation duct, or medical instrument.

7. The method in accordance with claim 6, wherein the object is a suspension media comprising at least one of a filter, electrostatic precipitator, or carbon bed.

8. The method in accordance with claim 1, wherein the plasma discharge device comprises a porous electrode.

9. A method of sterilizing or decontaminating a fluid to be treated using a plasma discharge device, comprising the steps of:
   introducing an additive fluid to the plasma discharge device, wherein the additive fluid comprises an organic compound;
   flowing the fluid to be treated through the plasma discharge device;
   producing a plasma generated active sterilizing species from the additive fluid and the fluid to be treated by operation of the plasma discharge device;
   exposing contaminants in the fluid to be treated to the plasma generated active sterilizing species;
   flowing the plasma generated active sterilizing species and the fluid to be treated downstream toward a suspension media;
   collecting particulate matter from the fluid to be treated in the suspension media; and
   exposing the particulate matter collected in the suspension media with to the plasma generated active sterilizing species.

10. The method in accordance with claim 9, further comprising the step of subjecting the fluid to be treated after passing through the suspension media to a catalyst media.

11. The method in accordance with claim 9, wherein the suspension media comprises at least one of a filter, electrostatic precipitator, or carbon bed.

12. The method in accordance with claim 10, wherein the suspension media comprises at least one of a filter, electrostatic precipitator, or carbon bed.

13. The method in accordance with claim 9, wherein the organic compound is an alcohol.

14. The method in accordance with claim 13, wherein the alcohol is ethanol or methanol.

15. The method in accordance with claim 9, wherein the plasma discharge device comprises a porous electrode.

16. The method in accordance with claim 7, further comprising the step of cleansing the particulate matter collected in the suspension media with the plasma generated active sterilizing species.

17. A method of producing active sterilizing species comprising the steps of:
   introducing an additive fluid into a plasma discharge device, wherein the plasma discharge device is adapted to receive the additive fluid, and wherein the additive fluid is a mixture comprising an organic vapor and air;
   producing a plasma generated active sterilizing species from the additive fluid by operation of the plasma discharge device; and
   emitting the plasma generated active sterilizing species from the plasma discharge device.

18. The method in accordance with claim 17, wherein the organic vapor is an alcohol.

19. The method in accordance with claim 18, wherein the alcohol is ethanol or methanol.

20. The method in accordance with claim 17, wherein the plasma discharge device has at least one of a capillary dielectric configuration, a slit dielectric, barrier discharge, and corona discharge configuration.

21. The method in accordance with claim 17, further comprising the step of exposing an object to the emitted active sterilizing species downstream from the plasma discharge device.

22. The method in accordance with claim 17, wherein the plasma discharge device comprises a porous electrode.

* * * * *